US010647593B2

(12) United States Patent
Takahashi et al.

(10) Patent No.: US 10,647,593 B2
(45) Date of Patent: May 12, 2020

(54) AMMONIA ADSORBENT

(71) Applicant: NATIONAL INSTITUTE OF ADVANCED INDUSTRIAL SCIENCE AND TECHNOLOGY, Tokyo (JP)

(72) Inventors: Akira Takahashi, Tsukuba (JP); Tohru Kawamoto, Tsukuba (JP); Parajuli Durga, Tsukuba (JP); Hisashi Tanaka, Tsukuba (JP); Yutaka Sugiyama, Tsukuba (JP); Yukiya Hakuta, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 311 days.

(21) Appl. No.: 15/315,911

(22) PCT Filed: Jun. 5, 2015

(86) PCT No.: PCT/JP2015/066301
§ 371 (c)(1),
(2) Date: Dec. 2, 2016

(87) PCT Pub. No.: WO2015/186819
PCT Pub. Date: Dec. 10, 2015

(65) Prior Publication Data
US 2017/0096348 A1 Apr. 6, 2017

(30) Foreign Application Priority Data
Jun. 6, 2014 (JP) ................................. 2014-118028

(51) Int. Cl.
*B01D 53/02* (2006.01)
*C02F 1/28* (2006.01)
(Continued)

(52) U.S. Cl.
CPC .......... *C02F 1/281* (2013.01); *B01J 20/0259* (2013.01); *B01J 20/04* (2013.01);
(Continued)

(58) Field of Classification Search
CPC .. B01J 20/0259; B01J 20/04; B01J 20/28007; B01J 20/3204; B01J 20/3212;
(Continued)

(56) References Cited

U.S. PATENT DOCUMENTS 3,023,623 A * 3/1962 Lang ....................... F23D 11/38
73/168
3,529,042 A * 9/1970 Lippert ............... C06B 21/0025
149/19.4
(Continued)

FOREIGN PATENT DOCUMENTS

CN 102762536 A 10/2012
JP 2005-263596 A 9/2005
(Continued)

OTHER PUBLICATIONS

Translation of JP2011-200856, Oct. 13, 2011, Aist.*
(Continued)

*Primary Examiner* — Christopher P Jones
(74) *Attorney, Agent, or Firm* — Manabu Kanesaka

(57) ABSTRACT

The object of the invention is to provide an adsorbent that can adsorb ammonia with no large volume change between absorption and desorption, that has a high ammonia and/or ammonium ion adsorption capacity, and that can have an additional function by gaining proper control of composition, etc. The invention makes it possible to provide an adsorbent that absorbs ammonia and/or ammonium ions through the use of a metal cyanocomplex as an ammonia adsorbent, experiences no or little volume change, exhibits high enough capacity for adsorbing ammonia and/or ammo-
(Continued)

nium ions, and has a function of decomposing ammonia as well as a function of varying optical responses before and after adsorption, etc.

14 Claims, 5 Drawing Sheets

(51) Int. Cl.
| | |
|---|---|
| *B01J 31/22* | (2006.01) |
| *C01C 3/11* | (2006.01) |
| *B01J 20/32* | (2006.01) |
| *B01J 20/04* | (2006.01) |
| *C01C 3/12* | (2006.01) |
| *B01J 20/28* | (2006.01) |
| *B01J 20/34* | (2006.01) |
| *B01J 20/02* | (2006.01) |
| *G01N 33/00* | (2006.01) |
| *C02F 101/16* | (2006.01) |

(52) U.S. Cl.
CPC ..... *B01J 20/28007* (2013.01); *B01J 20/3204* (2013.01); *B01J 20/3212* (2013.01); *B01J 20/3236* (2013.01); *B01J 20/3293* (2013.01); *B01J 20/3295* (2013.01); *B01J 20/3297* (2013.01); *B01J 20/3441* (2013.01); *B01J 20/3475* (2013.01); *B01J 31/22* (2013.01); *C01C 3/11* (2013.01); *C01C 3/12* (2013.01); *G01N 33/0054* (2013.01); *C02F 2101/16* (2013.01); *C02F 2303/16* (2013.01); *Y02A 50/246* (2018.01)

(58) Field of Classification Search
CPC B01J 20/3236; B01J 20/3293; B01J 20/3295; B01J 20/3297; B01J 20/3441; B01J 20/3475; B01J 31/22; C01C 3/11; C01C 3/12; C02F 1/281; C02F 2101/16; C02F 2303/16; G01N 33/0054; Y02A 50/246
See application file for complete search history.

(56) References Cited

U.S. PATENT DOCUMENTS

| | | | | |
|---|---|---|---|---|
| 3,729,413 | A | * | 4/1973 | Simo ................. C02F 1/281 |
| | | | | 210/725 |
| 3,830,753 | A | * | 8/1974 | Kondo ................. B01J 27/22 |
| | | | | 423/363 |
| 6,436,556 | B1 | * | 8/2002 | Bleck ................. C23C 2/006 |
| | | | | 428/681 |
| 7,988,766 | B2 | | 8/2011 | White et al. |
| 8,741,030 | B2 | | 6/2014 | Inubushi et al. |
| 8,865,615 | B2 | | 10/2014 | Ito et al. |
| 2007/0207351 | A1 | | 9/2007 | Christensen et al. |

FOREIGN PATENT DOCUMENTS

| | | |
|---|---|---|
| JP | 2007-531209 A | 11/2007 |
| JP | 2011-200856 A | 10/2011 |
| JP | 2012-200654 A | 10/2012 |
| JP | 2012-210570 A | 11/2012 |

OTHER PUBLICATIONS

China Patent Office, "Office Action for Chinese Patent Application No. 201580029894.X," dated Aug. 3, 2018.
Balmaseda, J. et al., "Behavior of Prussian blue-based materials in presence of ammonia," Journal of Physics and Chemistry of Solids, 2003, p. 685-693, vol. 64, Elsevier Science Ltd.
PCT/ISA/210, "International Search Report for PCT/JP2015/066301," dated Aug. 25, 2015.

* cited by examiner

AMMONIA ADSORBENT

RELATED APPLICATIONS

The present application is National Phase of International Application No. PCT/JP2015/066301 filed Jun. 5, 2015, and claims priority from Japanese Application No. 2014-118028, filed Jun. 6, 2014, the disclosure of which is hereby incorporated by reference herein in its entirety.

FIELD OF THE INVENTION

The present invention relates generally to an ammonia adsorbent, and more particularly to an ammonia adsorbent having the functions of occluding ammonia, decomposing ammonia, changes in optical responses, etc.

BACKGROUND OF THE INVENTION

Ammonia is a material that must direct attention to the importance of its management. Notably, ammonia attracts attention in the environment and energy fields. In the energy field, the synthesis of ammonia with the aid of renewable energy or the like is now considered. Optionally after stored in the form of chemical energy, the ammonia may be turned immediately into fuel or hydrogen may be removed out of the ammonia for fuel production (Patent Publication 1). In the field of biomass power generation, on the other hand, livestock's feces and urine or the like are fermented to turn methane into fuel, but most of the ensuing nitrogen content remains as ammonia in the digestive fluid, and how to make use of or process that ammonia is now under study (Patent Publication 2).

Meanwhile, a main ingredient of PM 2.5 that is a fine particle of less than 2.5 μm is known to be ammonia ions in the environmental field (Non-Patent Publication 1). A possible origin for this ammonia may be dissipations from farmlands, etc., and it is pointed out that stricter management may be applied to such dissipations from now on (Non-Patent Publication 2). Further, increased concentrations of ammonia in water may have an adverse influence on aquatic life; according to the established water criteria for fisheries, for instance, ammonia must have a very low concentration of as low as 0.01 mg/L for fresh water and 0.03 mg/L for seawater (Non-Patent Publication 3).

In other fields than the environmental and energy fields, a problem with ammonia is that it may remain as impurities in semiconductor productions and within fuel cells; there is a need for its removal. In addition, ammonia is often used for removal of nitrogen oxides out of exhaust gases; there is a challenge about how to address a problem arising from excessive addition of ammonia (for example, see Patent Publication 3).

Ways of how to manage such ammonia include exploitation of an ammonia adsorbent.

Ammonia adsorbents that have gained renown so far in the art are compounds including metals capable of forming ammine complexes such as calcium chloride (ammine complex-forming compounds, zeolite or similar materials.

In a possible process for occluding ammonia using an absorbent, ammonia is adsorbed onto the adsorbent, and pressures or temperatures are then controlled for dissipation of ammonia. However, the aforesaid ammine complex-forming compound changes largely in volume between the times of occlusion and desorption of ammonia, resulting in a problem that, for instance, even pulverization of that compound causes disintegration of particles as occlusion and desorption are repeated (Non-Patent Publication 4).

A problem with zeolite is on the other hand that volumes of adsorption are as low as 5 to 9 mmol (ammonium nitrogen per g of absorbent), although there have been studies of absorption behavior of ammonium ions in an aqueous solution. It is also impossible to provide them with additional functions of catalysis, changes in optical responses, and so on. Although there has been a detailed study of existing adsorbents described in Non-Patent Publication 5 about the adsorption of gaseous ammonia, the adsorption capability is only limited to 10 mmol/g at 100 kPa.

PRIOR ARTS

Patent Publications

Patent Publication 1: Japanese Unexamined Patent Application Publication No. 2007-5312029
Patent Publication 2: JP(A) 2012-200654
Patent Publication 3: JP(A) 2012-210570 Non-Patent Publications
Non-Patent Publication 1: K. KUMAYA, H. TAGO, A. IIJIMA, K. OZAWA, and K. SAKAMOTO, "Seasonal Properties of PC matters in plains and mountains in Gunma", JSAE, Vol. 45, No. 1 (2010), pp. 10-20
Non-Patent Publication 2: Eric STOKSTAD, "Ammonia Pollution From Farming May Exact Hefty Health Costs", Science, Vol. 343, pp. 238
Non-Patent Publication 3: Aquatic Water Standards (2005 edition)
Non-Patent Publication 4: T. ICHIKAWA, "Development of Compact, Transportable Ammonia Tanks", A Briefing for New Technology in Hiroshima University in Hiroshima, Oct. 17, 2013
Non-Patent Publication 5: Adsorption Equilibria of Ammonia Gas on Inorganic and Organic Sorbents at 298.15 K, Jarkko Helminen, Joni Helenius, and Erkki Paatero, Ilkkaturunen, J. Chem. Eng. Data, 2001, 46(2), pp. 391-399

SUMMARY OF THE INVENTION

Objects of the Invention

As described above, there is a material needed for ammonia adsorbents, which material makes sure stability such as no large change in volume upon adsorption of ammonia, and has a large adsorption capacity.

An ammonia adsorbent that further includes additional functions of catalysis and changes in optical responses will have a wider range of applications. For removal of ammonia out of gases such as the atmosphere, for instance, it is desired that the ammonia adsorbent used has a catalytic function of decomposition after adsorption of ammonia. Furthermore, if the adsorbent used is capable of bringing about changes in optical or electrical responses upon absorption of ammonia, it will also be able to be used in applications such as sensors.

With such situations in mind, the present invention has for its objects to provide an adsorbent that is capable of adsorbing ammonia with no or little changes in volume between absorption and desorption, and is capable of ensuring an increased volume of adsorption of ammonia or ammonium ions, and to provide an adsorbent material that makes it possible to provide it with additional functions such as catalysis and changes in optical responses through proper control of compositions, and so on.

Embodiments of the Invention

As a result of study after study, the present inventors have found that these objects are achievable by use of a metal cyanocomplex as an ammonia adsorbent. Further, the inventors have also obtained findings about the absorption behavior and additional functions of metal cyanocomplexes synthesized by various compositions and methods by carrying out proper testing of ammonia and/or ammonium ions.

The present invention has been accomplished on the basis of these findings, and is embodied as set forth below.

[1] An adsorbent for absorption of ammonia by contact with a medium containing ammonium ions or ammonia molecules, wherein a main composition of said adsorbent contains as an effective component a metal cyanocomplex represented by a general formula: $A_xM[M'(CN)_6]_y \cdot zH_2O$ where M stands for one or two or more metal atoms selected from the group consisting of vanadium, chromium, manganese, iron, ruthenium, cobalt, rhodium, nickel, palladium, platinum, copper, silver, zinc, lanthanum, europium, gadolinium, lutetium, barium, strontium, and calcium, M' stands for one or two or more metal atoms selected from the group consisting of vanadium, chromium, molybdenum, tungsten, manganese, iron, ruthenium, cobalt, nickel, platinum, and copper, A stands for one or two or more cations selected from the group consisting of hydrogen, lithium, sodium, potassium, rubidium, and cesium, x stands for a numerical value from 0 to 3, y stands for a numerical value from 0.1 to 1.5, and z stands for a numerical value from 0 to 6.

[2] An ammonia adsorbent as recited in [1], characterized in that a pressure is applied thereto upon contact of said adsorbent with an ammonia-containing gas thereby increasing an amount of adsorption.

[3] An ammonia adsorbent as recited in [1], characterized in that by contact of said absorbent with a liquid containing ammonia and/or ammonium ions, ammonia and/or ammonium ions are adsorbed thereto.

[4] An ammonia adsorbent as recited in any one of [1], [2] and [3], characterized in that by immersion of said adsorbent in water, an aqueous acid solution or an aqueous salt solution or irradiation of said adsorbent with ultraviolet rays, ammonia and/or ammonium ions are desorbed therefrom.

[5] An ammonia adsorbent as recited in any one of [1] to [4], characterized in that said adsorbent has a function of occluding ammonia at a reduction potential of +0 volt or lower on a hydrogen standard electrode basis.

[6] An ammonia adsorbent as recited in any one of [1] to [4], characterized in that said adsorbent has a catalytic function of decomposing the adsorbed ammonia at a reduction potential that is higher than −0.1 volt and lower than +1.5 volts on a hydrogen standard electrode basis.

[7] An ammonia adsorbent as recited in [6], characterized in that after decomposition of adsorbed ammonia, said adsorbed ammonia is left to stand in the atmosphere to restore said adsorbent back to a before-adsorption state.

[8] An ammonia adsorbent as recited in any one of [1] to [7], characterized in that there is a change in optical responses after and before absorption of ammonia and/or ammonium ions.

[9] An ammonia adsorbent as recited in any one of [1] to [8], characterized in that said absorbent is carried on a fiber or yarn, or a woven or unwoven fabric.

Advantages of the Invention

According to the present invention it is possible to provide an adsorbent for which the metal cyancomplex can be used to adsorb ammonia and/or ammonium ions with no large change in volume, making sure large enough capacity of absorption of ammonia and/or ammonium ions, and which has functions of occluding ammonia and decomposing ammonia and bringing about changes in optical responses such as light absorption spectra after and before adsorption of ammonia.

EMBODIMENTS FOR CARRYING OUT THE INVENTION

The present invention will now be explained at great length.

Unless otherwise stated, the "ammonia" referred to herein is understood to mean both $NH_3$ and $NH_4^+$. Take an aqueous solution as one example. There are both $NH_3$ and $NH_4^+$ in a ratio depending on pH; however, any form may be thought of as ammonia.

The "metalcyano complex" referred to herein is understood to have a composition represented by $A_xM[M'(CN)_6]_y \cdot zH_2O$, and when M and M' are identified, the complex is called an M-M' cyanocomplex. For example, when M=copper and M'=iron, the complex will be called a copper-iron cyanocomplex. The metal atom M used herein is preferably one or two or more metal atoms selected from the group consisting of vanadium, chromium, manganese, iron, ruthenium, cobalt, rhodium, nickel, palladium, platinum, copper, silver, zinc, lanthanum, europium, gadolinium, lutetium, barium, strontium, and calcium, among which one or two or more metal atoms selected from the group consisting of vanadium, chromium, manganese, iron, ruthenium, cobalt, nickel, copper, and zinc are more preferred, although one or two or more metal atoms selected from the group consisting of manganese, iron, cobalt, nickel, copper, and zinc are most preferred. The metal atom M' is preferably one or two or more metal atoms selected from the group consisting of vanadium, chromium, molybdenum, tungsten, manganese, iron, ruthenium, cobalt, nickel, platinum, and copper, among which one or two or more metal atoms selected from the group consisting of manganese, iron, ruthenium, cobalt, and platinum are more preferred, although one or two metal atoms selected from the group consisting of iron and cobalt are most preferred. A is one or two or more cations selected from the group consisting of hydrogen, lithium, sodium, potassium, rubidium, and cesium.

It is also noted that the metal cyanocomplex may further contain a solvent other than water, and a material that does not positively appear in its composition such as other ions serving as impurities.

Figure 1:
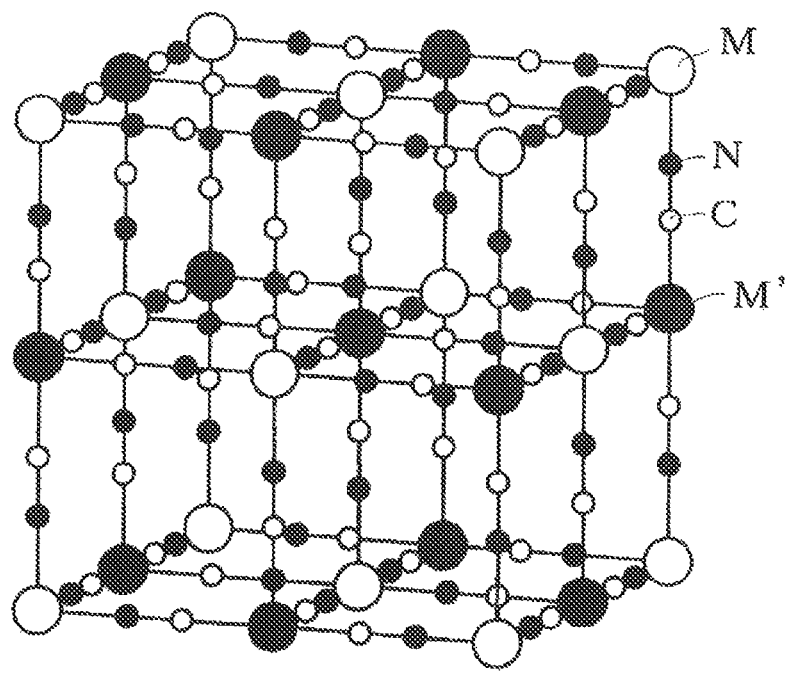
FIG. 1 is indicative of a typical crystal structure of a metal cyanocomplex.

By way of example but not by way of limitation, the metal cyanocomplex typically takes on such a face-centered cubic crystal structure as shown in FIG. 1. For instance, $K_{0.67}Zn[Fe(CN)_6]_{0.67} \cdot zH_2O$ takes the form of a hexagonal structure. While there are generally six cyano groups coordinated at M', it is to be understood that a part thereof may be replaced by a nitro group and coordination of 4 to 8 cyano groups does not give rise to any problem.

$NH_3$ is coordinated and adsorbed to an exposed metal site of the metal cyanocomplex with adsorption of $NH_4^+$ to a void site contained inside and having a size of 1 nm or less, and $NH_3$ may possibly be adsorbed to the void site as well. Such adsorption does not involve a large volume change due to adsorption and desorption, because there is no large influence on its crystal structure unlike a metal ammine complex so that the aforesaid objects are achievable.

The subscript x is preferably from 0 to 3, more preferably from 0 to 2.5, and most preferably from 0 to 2, and the subscript y is preferably from 0.1 to 1.5, more preferably from 0.4 to 1.3, and most preferably from 0.5 to 1. The subscript z is preferably from 0 to 6, more preferably from 0.5 to 5.5, and most preferably from 1 to 5.

Referring to the subscripts x, y and z, however, it is to be noted that when salts are contained as impurities and the material used includes moisture not entrapped in the internal structure of a Prussian blue type complex, for instance, estimation must be made while factoring out their effect.

It is here to be noted that depending on which one of $NH_3$ and $NH_4^+$ is mainly to be adsorbed, the preferable range of the value of y in particular varies. A smaller y means that the content of $[M'(CN)_6]$ in the crystal gets smaller; the metal M will be excessive as compared with $[M'(CN)_6]$, in which case ligands are likely to be adsorbed to around the metal M, ending up with an increase in the amount of adsorption of $NH_3$ in particular.

Referring to the desired particle diameter of the metal cyanocomplex, it is often generally said that the higher the specific surface area of the material, the faster the adsorption takes place. From this point of view, the primary average particle diameter is preferably 500 nm or lower, more preferably 300 nm or lower, and most preferably 100 nm or lower. Although there is no particular restriction on the lower limit of the particle diameter, it is practically advantageous that the particle diameter is 4 nm or more. The "primary particle diameter" used herein is understood to refer to the diameter of primary particles. To this end, the equivalent circle diameter may be derived from the peak half-width found by powder X-ray structural characterizations. There is sometimes adsorption of ligands or the like to the surfaces of particles; in this case, the primary particle diameter is provided while the ligands are eliminated.

There is no particular limitation on how to synthesize metal cyanocomplexes; however, preference is given to a method by which the desired composition can uniformly be obtained. For the sake of processing, the complex may be modified on its surface with various materials. Particular methods available to the end are disclosed typically in JP(A)'s 2006-256954 and 2013-173077. Nanoparticles having large specific surface areas are more desired because ammonia may be adsorbed to the metal site exposed on the surfaces of particles too. It is practically desired for particles to be uniform or even; it is suitable to make use of a method for producing uniform nanoparticles such as the one disclosed in JP(A) 2013-173077.

Even with the adsorbent composited with other material(s) for various reasons, there is no problem arising as long as it contains the metal cyanocomplex and functions as an ammonia adsorbent. For instance, it may be carried on a fiber or yarn, or a woven or unwoven fabric or, alternatively, it may be mixed with a binder such as a polymer in a particulate state. To allow for efficient development of catalytic effect, the adsorbent may further be composited with oxidizing agents, reducing agents, electrically conductive materials, and so on.

Referring to the adsorption function, the adsorbent may occlude ammonia inside under some conditions with a volume change of 20% or less. For instance, the absorbent may include ammonia upon application of a pressure and release off it upon removal of that pressure or, alternatively, the adsorbent may adsorb ammonia at normal temperatures under normal pressures and release off it upon heating.

For occlusion of ammonia by application of a pressure, that pressure is preferably 8 atm or less, more preferably 5 atm or less, and most preferably 2 atm. When the adsorbed ammonia is released off by temperature, there is no particular limitation unless the adsorbent is decomposed or otherwise denatured by heating. Generally, that temperature is preferably 300° C. or lower, more preferably 250° C. or lower, and most preferably 200° C. or lower.

When used as an occluding material, both the adsorbent and ammonia must remain chemically stable even with ammonia adsorbed to it. A potential at which ammonia is oxidized into nitrogen molecules is about +0.1 volt to about +0.3 volt on the standard hydrogen electrode basis; the reduction potential for the adsorbent is by far higher than that potential. Here take a copper-iron cyano-complex as an example. The redox (oxidation-reduction) potential for iron between divalency and trivalency is roughly about +1.0 volt; use of a copper-iron (III) cyano-complex containing trivalent iron may lead to a likelihood of ammonia being oxidized and decomposed. In contrast, use of a copper-iron (III) cyanocomplex containing divalent iron makes it possible to maintain both ammonia and the adsorbent in a stable state without any oxidization of ammonia by the adsorbent.

From this, it is found that when the metal cyano-complex is used as an occluding material, the reduction potential is higher than preferably +0.3 volt, more preferably +0.5 volt, and most preferably +0.7 volt on the standard hydrogen electrode basis. As long as this requirement is satisfied, there is no limitation on the type of cyanocomplexes; for instance, there is the mention of zinc-iron, copper-iron, and manganese-iron cyanocomplexes.

When the adsorbent has an additional function of decomposing ammonia after adsorption, on the other hand, the reduction potential for the adsorbent must be equivalent to or lower than the oxidation potential for ammonia. Here take an iron-iron cyanocomplex as an example. If the initial state is an iron (III)-iron (II) cyanocomplex, the reduction potential is then +0.3 volt to +0.4 volt at which the cyanocomplex itself may be reduced for oxidation and decomposition of ammonia. Further, in the atmosphere or water containing oxygen, the reduction potential for oxygen molecules is about +0.4 volt to about −0.2 volt although depending on a situation of measuring the reduction potential for oxygen molecules so much so that the iron-iron cyanocomplex reduced in the process of decomposition of ammonia is again oxidized by oxygen. It follows that the iron (III)-iron (II) cyanocomplex can function as a catalyst for decomposition of ammonia. As this is written by reaction or semi-reaction formulae, the following reactions are expected to occur.

1. Decomposition of Ammonia $$2NH_3 \Leftrightarrow N_2 + 6H^+ + 6e^- (0.1V\ VS\ SHE)$$

$$Fe^{III}[Fe^{II}(CN)_6]_{0.75} + H^+ + e^- \Leftrightarrow HFe^{II}[Fe^{II}(CN)_6]_{0.75} (+0.3V\ VS\ SHE)$$

That is, $$2NH_3 + 6Fe^{III}[Fe^{II}(CN)_6]_{0.75} \Leftrightarrow N_2 + 6HFe^{II}[Fe^{II}(CN)_6]_{0.75}$$

2. Restoration of the Cyanocomplex State $$HFe^{II}[Fe^{II}(CN)_6]_{0.75} \Leftrightarrow Fe^{III}[Fe^{II}(CN)_6]_{0.75} + H^+ + e^- (+0.3V\ VS\ SHE)$$

$$O_2 + 4H^+ + 4e^- \Leftrightarrow 2H_2O (+1.2V\ VS\ SHE)$$

That is, $$4HFe^{II}[Fe^{II}(CN)_6]_{0.75} + O_2 \Leftrightarrow 4Fe^{III}[Fe^{II}(CN)_6]_{0.75} + 2H_2O$$

In summary, all the reactions may be wrapped up in a reaction: $4NH_3 + 3O_2 \Leftrightarrow 2N_2 + 6H_2O$, in which case the iron-iron cyanocomplex behaves as a catalyst. To make this reaction occur, the reduction potential for the metal cyanocomplex must be higher than the oxidation potential for ammonia and lower than the reduction potential for oxygen. However, the redox potential varies largely depending on surrounding environments, meaning that it is not always necessary to meet this condition entirely. From the foregoing, it is found that the reduction potential for the metal cyanocomplex is preferably higher than +0.1 volt and lower than +1.5 volts, more preferably higher than +0.1 volt and lower than +1.2 volts, and most preferably higher than +0.3 volt and lower than +1.0 volt. There is no limitation on metal complexes as long as they satisfy this requirement; for possible particular materials, there is the mention of nickel-iron cyanocomplexes in addition to the iron-iron cyanocomplexes.

Further, if there is a change in the optical response of the cyanocomplex in association with adsorption of ammonia, it may be used as an ammonia sensor or the like. There is no limitation on why the optical response changes; however, there are actually changes in absorption spectra because the metal cyanocomplex is reduced upon development of, for instance, the aforesaid catalytic function. Coordination of ammonia at the metal M causes a change in the surrounding environment of the metal M, which triggers a change in the optical response too.

EXAMPLES

By way of example but not by way of limitation, the present invention will now be explained in further details with reference to some examples.

Preparation Example 1—Preparation of the Copper-Iron Cyanocomplex

A copper-iron cyanocomplex $(K_2Cu_3[Fe(CN)_6]_2)$ was prepared as described below.

Copper sulfate pentahydrate (18.7 g) was dissolved in pure water in such a way as to provide 500 mL of an aqueous solution having a copper ion concentration of 0.15 mole/L. Apart from this, 21.1 grams of potassium ferrocyanide trihydrate were dissolved in pure water in such a way as to provide 500 mL of an aqueous solution having a ferrocyanide ion concentration of 0.10 mole/L. The cyanocomplex was synthesized in a flow process having a flow rate adjusted to 94 mL/min. In this example, there was an assembly used in which a flow passage portion of a Y-shaped micromixer [1/16 Y PEEK, Product Code: MY1XCPK (MicroVolume Connector made by VICI)] was joined to a connector portion of [1/16 Y SUS, Product Code: MY1XCS6], with a liquid density of 1100 kg/m$^3$, a pipe diameter of $1.5 \times 10^{-4}$ m and a viscosity of $2 \times 10^{-3}$ Pa/s.

Three hundred (300) mL of the obtained liquid were desalinated with the aid of a cross-flow filter using 8 L of MilliQ water. The obtained precipitates were washed with pure water and then vacuum dried to obtain reddish brown powders PCu1.

As a result of estimation of the obtained PCu1 by an X-ray diffractometer, it has been found that there is a match for the $K_2Cu_3[Fe(CN)_6]_2$ peak position in the date base.

The average primary particle diameter of the obtained PCu1 was found to be about 11 nm by application of the Scherrer equation to the peak width in powder X-ray diffractions. The Scherrer equation here is represented by $d = K \times \lambda/(\beta \times \cos \theta)$ where d is the primary particle diameter, K is the Scherrer constant (0.94), $\lambda$ is the wavelength of X-rays, and $\theta$ is the diffraction angle of the peak.

Further, the composition of powders PCu1 was estimated by the following method. Fifty (50) mg of powders PCu1 were added to 4 mL of hydrochloric acid and 2 mL of nitric acid, and the resulting solution was subjected to microwave digestion using a microwave digester (Multiwave 3000 made by PerkinElmer Co., Ltd.), after which K, Cu and Fe were quantitated using ICP-MS (NEXION 300D made by PerkinElmer). Quantitative determination of C and N was carried out by light element analysis while H$_2$O was quantitated by thermogravimetry. Consequently, PCu1 was determined to have a composition: $K_{0.68}Cu[Fe(CN)_6]_{0.65} \cdot 3.2H_2O$.

Preparation Example 2—Preparation of the Copper-Iron Cyanocomplexes with Varying Composition Ratios The same method as in Preparation Example 1 was repeated except that the concentrations of copper sulfate solution and potassium ferrocyanide were changed as set out in Table 1 thereby obtaining powders PCu2, PCu3 and PCu 4 of the copper-iron cyanocomplexes. The results of analysis of their compositions are also shown in Table 1.

TABLE 1

|  |  | PCu1 | PCu2 | PCu3 | PCu4 |
|---|---|---|---|---|---|
| Starting Materials | Cu Ion Conc. (mol/L) | 0.15 | 0.16 | 0.17 | 0.20 |
|  | Ferrocyanide Ion Conc. (mol/L) | 0.10 | 0.10 | 0.10 | 0.10 |
| Compositions of Adsorbents | x | 0.68 | 0.47 | 0.34 | 0.06 |
|  | y | 0.65 | 0.61 | 0.57 | 0.52 |
|  | z | 3.17 | 3.80 | 3.98 | 4.55 |

Preparation Example 3—Preparation of the Manganese-Iron Cyanocomplex

A manganese-iron cyanocomplex was synthesized as described below.

A manganese-iron cyanocomplex ($Mn_3[Fe(CN)_6]_2$) was prepared as described below.

Nine point nine (0.90) gram of manganese chloride tetrahydrate was dissolved in pure water in such a way as to provide 500 mL of an aqueous solution having a manganese ion concentration of 0.10 mol/L.

Apart from this, 3.30 grams of potassium ferricyanide were dissolved in pure water in such a way as to provide 100 mL of an aqueous solution having a ferricyanide ion concentration of 0.10 mol/L. Mixing of these liquids resulted in brown precipitates that were then washed with MilliQ water five times. Thereafter, the precipitates were dried by evaporation into brown powders PMn1. As a result of estimation as in Example 1, PMn1 has been found to have a composition $Mn[Fe(CN)_6]_{0.67} \cdot 4.0H_2O$.

Preparation Example 4—Preparation of the Iron-Iron Cyanocomplex

Potassium ferrocyanide trihydrate (25.3 grams) and iron nitrate enneahydrate (22.4 grams) were each dissolved in 500 mL of ultrapure water to obtain solutions that were then mixed together a 250 μm-micromixer at a rate of 50 mL/min. to prepare a suspension containing an iron-iron cyanocomplex. The iron-iron cyanocomplex in the suspension was separated by centrifugation from a supernatant liquid followed by washing with ultrapure water six times. After the washings, the resulting precipitates were vacuum dried for 2 days into a dried matter that was then pulverized thereby obtaining 23 grams of iron-iron cyanocomplex PFe1. As a result of analysis of the prepared iron-iron cyanocomplex (precipitates) by a powder X-ray diffractmeter, there was a match for the iron-iron cyanocomplex: $Fe_4[Fe(CN)_6]_3$ retrieved from the standard sample data base. Further, FT-IR measurement has also showed that there is a peak appearing near 2080 cm-1 resulting from Fe—CN stretching vibration, indicating that this solid was an iron-iron cyanocomplex having a particle diameter of about 10 to about 20 nm measured by a transmission electron microscope.

Preparation Example 5—Preparation of the Water-Dispersible Iron-Iron Cyanocomplex PFe1, obtained as mentioned above, was weighed out in an amount of 2.298 grams in a snap vial, and 0.887 gram of potassium ferrocyanide trihydrate was placed in that snap vial, after which ultrapure water was placed in the snap vial in a total amount of 40 grams to prepare a surface-treatment suspension. Using an ultrahigh speed centrifuge, the suspension was washed five times under conditions of 90,000 G and 30 minutes to remove a portion of potassium ferrocyanide not used for surface treatment, and the ensuing precipitates were vacuum dried for one day just as they were, and pulverized and dried to obtain a water-dispersible iron-iron cyanocomplex PFe2.

Preparation Example 6—Preparation of the Water-Dispersible Iron-Iron Cyanocomplex Thin Film To confirm that the inventive adsorbent has an additional catalytic effect and brings about a change in optical responses, and that the inventive adsorbent allows for the iron-iron cyanocomplex to regain its original color not only in the atmosphere but also in water or an aqueous acid solution, iron-iron cyanocomplex PFe2 obtained in Preparation Example 5 was used to make an iron-iron cyanocomplex thin film as described just below.

First of all, 1 gram of PFe2 was suspended in 10 mL of ultrapure water to turn the water into a blue transparent solution. That solution was added dropwise onto a quartz substrate located on a spin coater for a 10-seconds spin coating at 1400 rpm and a 10-seconds spin coating at 2000 rpm. As a result, there was a PB (Prussian blue) thin film FFe2 obtained in blue.

Then, the obtained PB thin film was immersed in 0.1 mmol/L of an aqueous iron nitrate solution thereby obtaining a PB thin film FFe2-2 rendered insoluble in water.

Preparation Example 7—Preparation of the Iron-Iron Cyanocomplex/Cellulose Composite Material A cellulose fabric (BEMCOT; Asahi KASEI) was impregnated with a dispersion of 100 mg of PFe2 of Preparation Example 5 dissolved in 1 mL of ultrapure water, and dried at 50° C. for 30 minutes thereby obtaining a cellulose fabric PBC having Prussian blue carried on it.

Preparation Example 8—Preparation of the Cobalt-Cobalt Cyanocomplex

A solution of 1.329 grams of potassium hexacyanocobaltate dissolved in 0.1 L of ultrapure water and a solution of 1.428 grams of cobalt chloride hexahydrate dissolved in 0.1 L of ultrapure water were mixed together in a beaker, and stirred by a magnetic stirrer overnight, after which the mixture was centrifuged at 16,000 G for 10 min. thereby obtaining precipitates. Ultrapure water was added to the precipitates, and washing was likewise carried out by centrifuging a supernatant liquid from the precipitates and throwing away the supernatant. Like washing was repeated five times to obtain precipitates PCo1. From XRD patterns, PCo1 has been found to have a crystal structure similar to $Co[Co(CN)_6]_{0.67}$.

Example 1—Adsorption of $NH_3$ by the Copper-Iron Cyanocomplex from an Aqueous Ammonia Solution Then, there was solution L1 provided as an adsorption testing solution in which 0.1 mol/L of ammonium chloride and 0.1 mol/L of ammonia water were mixed together. After 50 mg of PCu1 obtained in Preparation Example 1 were immersed in 5 mL of L1, solid-liquid separation was allowed to take place to find the amount of $NH_3$ remaining in the liquid. For the shaking apparatus or shaker, there was SI-300C (made by AS ONE Corporation) used that was put into operation under conditions involving a shaking rate of 1,800 rpm, a temperature of 25° C. and a shaking time of 3 hours.

Centrifugal separation was applied for the solid-liquid separation under conditions involving a combined 3,000 G and 3 minutes, and a combined 12,000 G and 15 minutes.

The quantity of $NH_3$ was determined by means of back titration using sulfuric acid: the method for determining the quantity of $H^+$ in the liquid thereby making estimation of the amount of $NH^3$ in the sample liquid. Back titration was carried out by diluting 97% by weight sulfuric acid down to 40 mmol/L of a dilute sulfuric acid and mixing 10 mL of this dilute sulfuric acid with 1 mL of a sample liquid. A titrator (COM-1750, Hiramuma Sangyo Co., Ltd.) was used for neutralization titration involving addition of sodium hydroxide, wherein the point of neutralization was detected using the maximal value of a pH electrode potential change ($\Delta E/\Delta mL$) relative to the amount of the sodium hydroxide added. As a result, the amount of absorption of $NH_3$ by powder PCu1 was estimated to be 2.3 mmol (ammonium nitrogen)/g (absorbent).

Example 2—Adsorption of $NH_3$ from Aqueous Ammonia Solutions by Copper-Iron Cyanocomplexes Having Varying Composition Ratios For PCu2, PCu3 and PCu4 obtained in Preparation Example 2 too, $NH_3$ absorption testing was carried out as in Example 1 to make estimation of the amount of adsorption.

Figure 2:
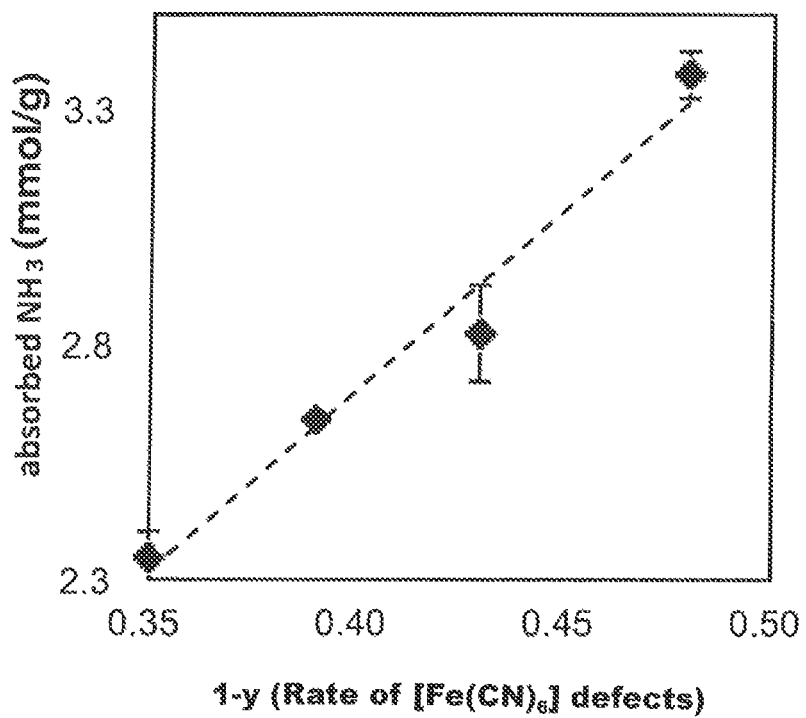
FIG. 2 is indicative of the 1-y dependency of the amount of adsorption of $NH_3$ by a copper-iron cyanocomplex.

The results of PCu1 to PCu4 are illustrated in FIG. 2 showing that the amounts of adsorption of $NH_3$ have linear relations to 1−y. In this case, 1−y is indicative of the rate of $[Fe(CN)_6]^{4-}$ ion defects in the absorbent; the larger y, the less the defects will be and the less the coordinate site for adjoining copper ions will be. This would suggest that the adsorbed $NH_3$ sits at the coordinate site for copper ions.

Example 3—Desorption of $NH_3$ from the Copper-Iron Cyanocomplex and Manganese-Iron Cyanocomplex by Heating PCu1 obtained in Example 1 with $NH_3$ absorbed onto it was dried to obtain PCu1A. $NH_3$ was absorbed onto PMn1 obtained in Preparation Example 3 as in Example 1, after which it was dried to obtain PMn1A. Desorption of $NH_3$ from these samples by heating was carried out by means of thermogravimetry, for which TG-DTA (Thermo plus EV0II made by Rigaku Co., Ltd.) was used to make estimation of PCu1A and PMn1A each in an amount of 10 mg. The results are depicted in FIG. 3.

Figure 3:
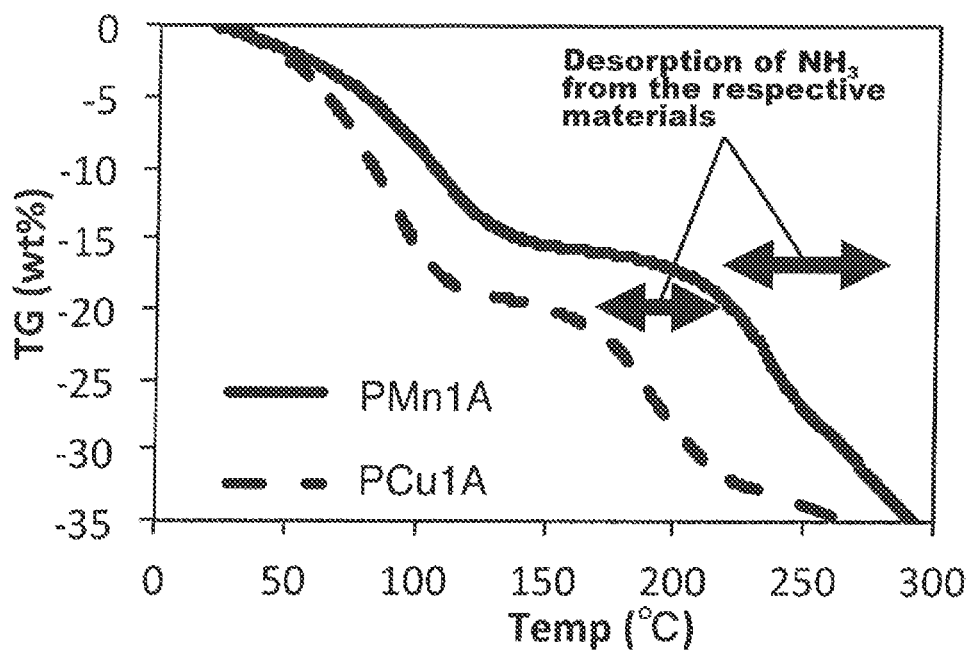
FIG. 3 is indicative of a thermogravimetric change by heating of a manganese-iron cyanocomplex and a copper-iron cyanocomplex after absorption of $NH_3$.

As shown by double action arrows in FIG. 3, PCu1A and PMn1A were reduced in weight in the vicinity of 150° C. to 200° C. and 200° C. to 250° C., respectively.

Apart from this, it has actually been confirmed that such weight reductions were ascribable to $NH_3$. After 50 mg of PMn1A were filled in a stainless tube, a muffle furnace was held at 220° C. for 20 minutes. In the meantime, a diaphragm pump was used to feed an air at 50 mL/min. The ensuing gas was recovered with sulfuric acid in an impinger. Use was made of a sulfuric acid in an amount of 100 mL and 4 mmol/L. The amount of $NH_3$ recovered from neutralization titration of sulfuric acid after experimentation was conclusively found to be 0.7 mmol/L in concentration. This has showed that heating makes desorption of adsorbed $NH_3$ possible.

Figure 4:
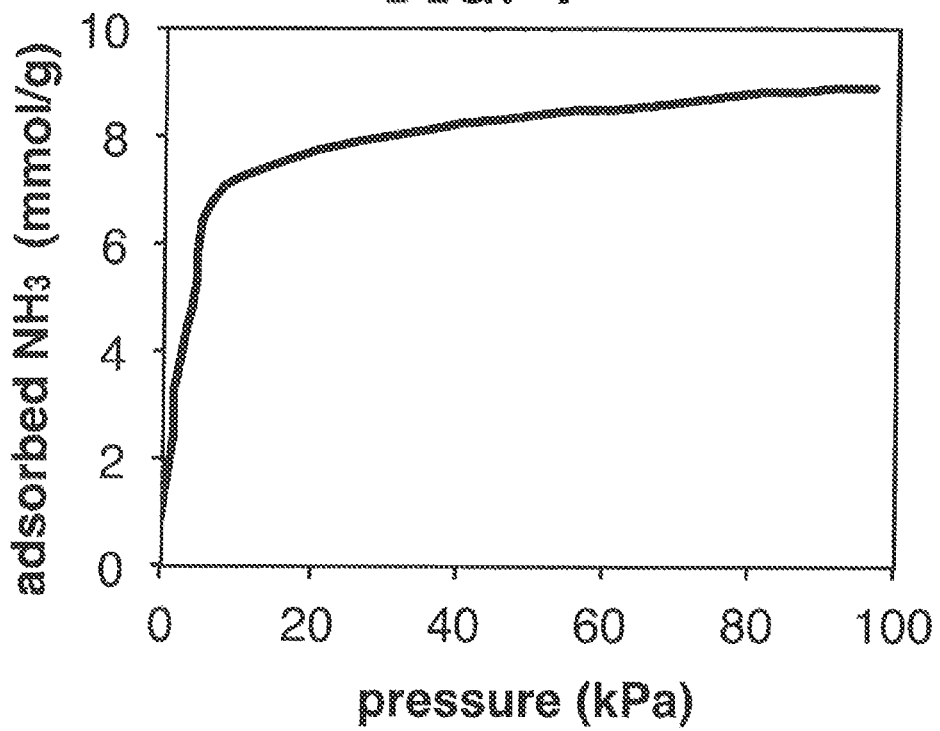
FIG. 4 is indicative of the pressure dependency of $NH_3$ absorption behavior of a manganese-iron cyano-complex.

Example 4—Dependency of Ammonia Gas Adsorption Pressure on the Manganese-Iron Cyanocomplex To confirm the dependency of ammonia gas on the pressure adsorption, ammonia gas adsorption testing was carried out using manganese-iron cyanocomplex PMn1 obtained in Preparation Example 3. Used to this end was a gas adsorption apparatus (BELSORP-max made by Nippon Bell Co., Ltd.). Prior to measurement, PMn1 was heated to and at 150° C. for 12 hours while evacuated for dehydration, after which ammonia gas was put in to observe pressure changes thereby confirming the dependency of the amount of adsorption on pressure. The results are illustrated in FIG. 4. $NH_3$ adsorbed up to 10 kPa was 7.5 mmol (ammonia)/g (adsorbent); this is roughly in agreement with the notion that $NH_3$ was adsorbed onto the metal M exposed in PMn1. In other words, adsorption at 10 kPa or higher would appear to take place at void sites rather than via coordination to the metal M, indicating that $NH_3$ was adsorbed by pressurization onto the void sites too.

Example 5—Adsorption of $NH_3$ onto the Iron-Iron Cyanocomplex and its Catalytic Effect In this example, the PB thin film FFe2 obtained in Preparation Example 6 was used to confirm that the iron-iron cyanocomplex makes sure an additional catalytic effect and brings about a change in optical responses.

PF thin film FFe2 was set in UV-Vis flow cell having a structure with a gas flow passage sandwiched between quartz plates, and $NH_3$ gas was flowed at a concentration of 200 ppm and a flow rate of 5 mL/min through the flow cell for measurements using a UV-Vis spectrometer (USB-4000: Ocean Optics Inc.).

Figure 5:
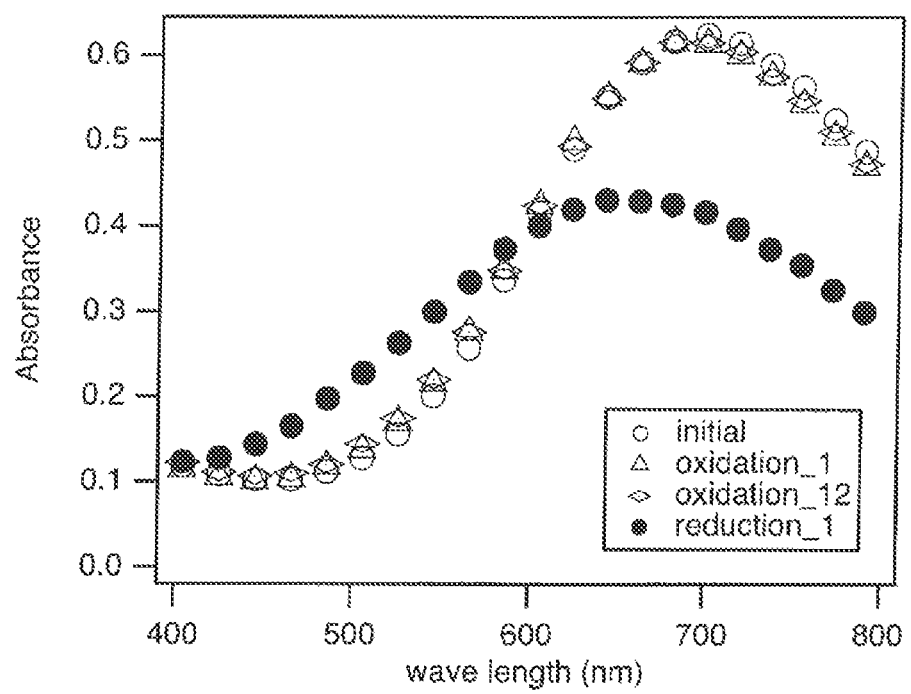
FIG. 5 is indicative of an absorbance change in a UV-Vis region upon contact of $NH_3$ gas with an iron-iron cyano complex.

Absorbance changes in the UV-Vis region upon contact of $NH_3$ gas with iron-iron cyanocomplex PFe2 are shown in FIG. 5 in which spectra -○- and -●- are indicative of absorption peaks before and after 700 nm in an initial state before contact with ammonia gas and after the first contact with ammonia gas, respectively. As a result of leaving this to stand in the atmosphere for 2 days, there was a change to a spectrum -Δ-, indicating that it went back to the peak indicated by -○- before the contact with ammonia gas. This would be due presumably to the fact that after adsorption of ammonia, a part of the iron-iron cyanocomplex was reduced, simultaneously with decomposition by oxidation of ammonia, into achromic transparency, and returning back to the original color after two days would be due to the fact that the original state is restored by atmospheric air.

A mark -◇- in FIG. 5 is indicative of an absorption spectrum after 12 repetitions of similar testing; that is, treatment of ammonia by the iron-iron cyanocomplex and restoration of the iron-iron cyanocomplex by the atmosphere could be repeated 12 times with high reproducibility. It has thus been found that the iron-iron cyanocomplex can function as an oxidation catalyst for ammonia.

Example 6—Recycling of the Adsorbent by Immersion in Water

In this example, PB thin film FFe2-2 obtained in Preparation Example 6 and rendered insoluble in water was used to confirm that the iron-iron cyanocomplex after adsorption of ammonia can be restored back to its original color even by water washing.

Figure 6:
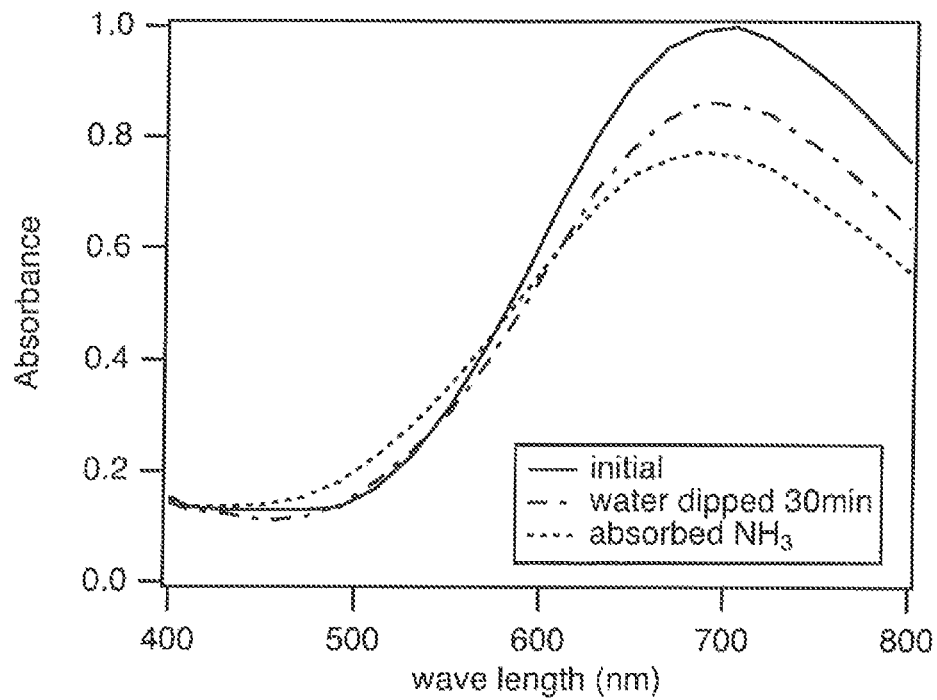
FIG. 6 is indicative of an absorbance change in a UV-Vis region upon contact of an iron-iron cyanocomplex with water after adsorption of ammonia.

PB thin film FFe2-2 was placed in a closed container replaced inside by dry air, and 5 mL of ammonia gas were poured in it. As a result, there was a decrease in the 700-nm absorption peak that the iron-iron cyanocomplex had, as indicated by a dotted line ( . . . ) in FIG. 6. After that, PB thin film FFe2-2 obtained in Preparation Example 6 with a color change by ammonia was immersed in ultrapure water. As a result, the 700-nm absorption peak was restored back to the original color, as indicated by a dashed line (-•-) in FIG. 6.

Example 7—Recycling of the Adsorbent by an Acid

PB thin film FFe2-2 obtained in Preparation Example 6 was left to stand in a flask having a volume of 1.5 L and an ammonia concentration of 200 ppm for 5 minutes for adsorption of ammonia, followed by measurement by a Fourier transform infrared spectrophotometer (FTIR). As a result, there was a peak increase at 1400 cm$^{-1}$ that would appear to be ascribable to ammonia, as indicated by a dotted line ( . . . ) in FIG. 7.

Figure 7:
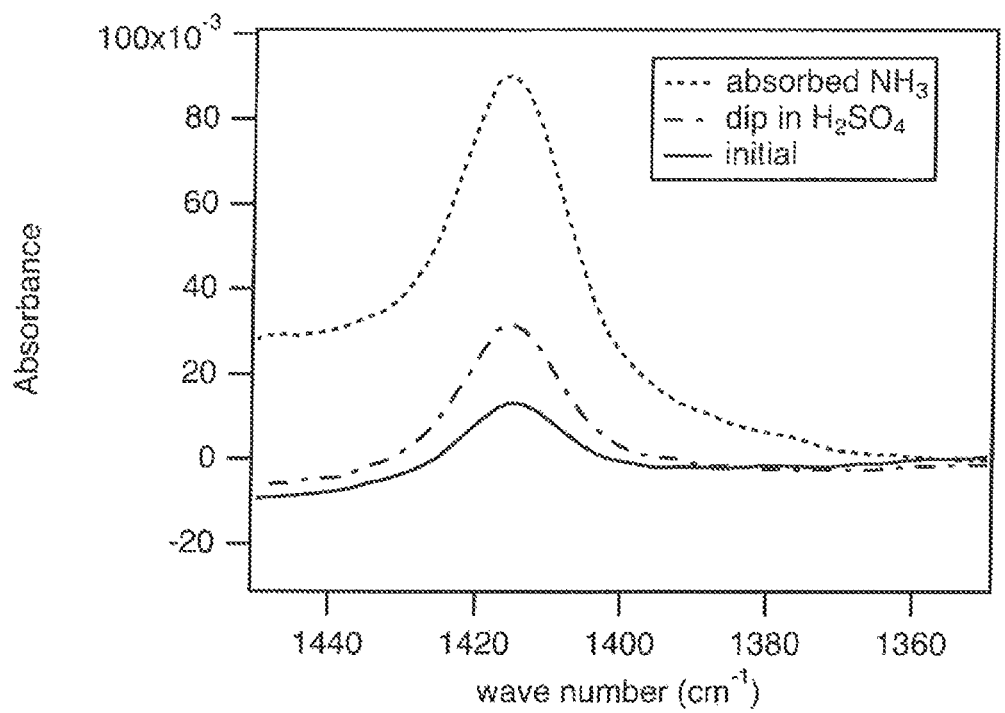
FIG. 7 is indicative of an infrared absorbance change upon contact of an iron-iron cyanocomplex with a dilute acid aqueous solution after adsorption of ammonia.

Then, this thin film having ammonia adsorbed onto it was immersed in 0.5 mmol/L of sulfuric acid with the result that there was a decrease in the 1400 cm$^{22}$ peak as indicated by a dashed line (-•-) in FIG. 7, from which desorption of ammonia by the acid was confirmed.

From this it has been found that the immersion in acid of PB having ammonia adsorbed to it, too, makes it possible to recycle PB as an ammonia adsorbent.

Example 8—Recycling of the Adsorbent by Irradiation with Ultraviolet Rays

Figure 8:
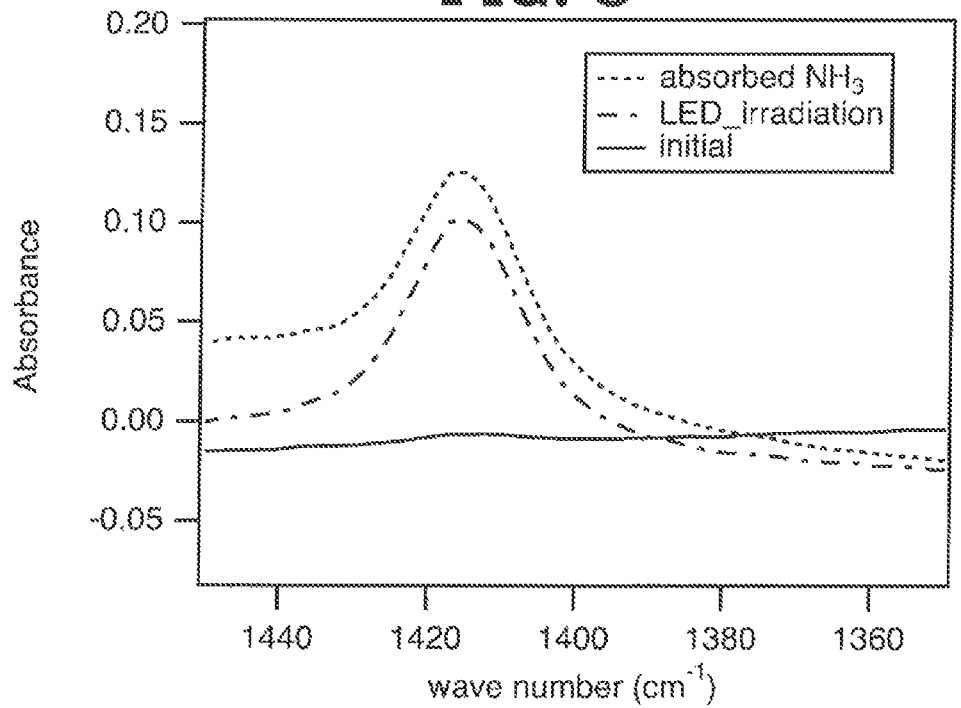
FIG. 8 is indicative of an infrared absorbance change upon irradiation of an iron-iron cyaocomplex with ultraviolet rays after adsorption of ammonia.

PB thin film FFe2-2 obtained in Preparation Example 6 was left to stand in a flask having a volume of 1.5 L and an ammonia concentration of 200 ppm for 5 minutes for adsorption of ammonia, followed by measurement by FTIR. As a result, there was a peak increase at 1400 cm$^1$ that would appear to be ascribable to ammonia, as indicated by a dotted line ( . . . ) in FIG. 8.

Then, this PB thin film having ammonia adsorbed onto it was irradiated with ultraviolet rays from UV-LED (UJ20 made by Panasonic Corp.) having an intensity of 150 mW/cm$^2$ and set at a 4 cm-away position. As a result, there was a decrease in the 1400 cm-1 peak, as indicated by a dashed line (-•-) in FIG. 8, from which desorption of ammonia by irradiation with ultraviolet rays was confirmed. From this, it has been found that irradiation with ultraviolet rays, too, makes desorption and recycling of the PB thin film possible.

Example 9—Adsorption of $NH_4^+$ onto the Copper-Iron Cyanocomplex

PCu1 obtained in Preparation Example 1 was used to confirm the adsorption of $NH_4^+$ in an aqueous solution. An aqueous solution of ammonium chloride L2 was prepared in such a way as to have an ammonium nitrogen concentration of 10 mg/L. Then, 40 mg of PCu1 were immersed in 40 mL of L2, and shaking was carried out at 30° C. for 6 hours, after which solid-liquid separation took place to estimate the concentration of $NH_4^+$ in the solution by means of total nitrogen measurement. The concentration of $NH_4^+$ went down to 76%, leading to the confirmation of adsorption of $HN_4^+$. From this, it has been found that the metal cyanocomplex allow for adsorption of both $NH_3$ and $NH_4^+$.

Example 10—Desorption of $NH_4^+$ by Saline Water from the Copper-Iron Cyanocomplex Having $NH_4^+$ Adsorbed onto it As in Example 9, 40 mL of a 0.1M KCl solution were added to 40 mg of a copper-iron cyanocomplex having ammonia adsorbed to it in an amount of 10.15 mg (nitrogen)/g (copper-iron cyanocomplex), and then shaken at 30° C. for 2.5 hours, resulting in elution of 66% ammonium ions. This has shown that saline water could be used for desorption of ammonium from the copper-iron cyano complex.

Example 11—Support of the Iron-Iron Cyanocomplex on a Cellulose Fabric and Adsorption of Ammonia Cellulose fabric PBC obtained in Preparation Example 7 and having PB supported or carried on it was filled or packed in a column of 15 mm in inner diameter and 61.5 mm in length, through which 57 L of dry air containing 0.87 ppm of $NH_3$ were passed from a gas bag at a flow rate of 1 L/min. The ammonia in the gas after passing through the column was trapped in 5 g/L of an aqueous solution of boric acid for estimation purposes. Ninety-six (96) % of ammonia in the gas were adsorbed by the column, indicating that the ability of Prussian blue to adsorb ammonia could be used even in a composite form.

Example 12—Adsorption of Ammonia onto the Cobalt-Cobalt Cyanocomplex

A metal other than iron may also be used for the metal that is coordinated on the carbon side of the cyano group.

Figure 9:
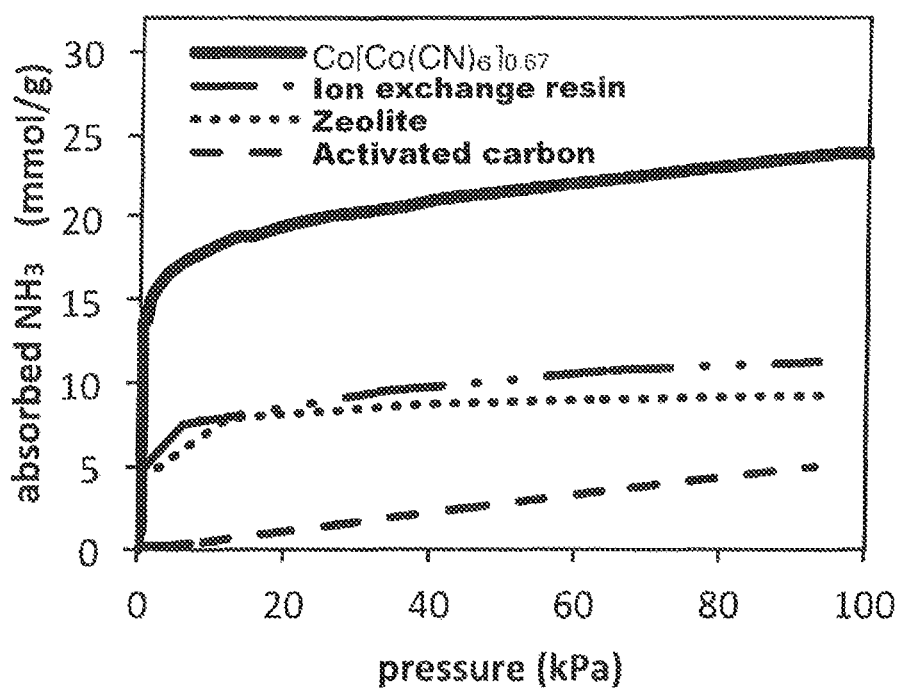
FIG. 9 is indicative of an isothermal curve of adsorption of ammonia by a cobalt-cobalt cyanocomplex.

Here take the cobalt-cobalt cyanocomplex PCo1 obtained in Preparation Example 8 as an example for estimation of isothermal adsorption curves. Specifically, a gas adsorption apparatus (BELSORP-max made by MicroTrack Bell Co., Ltd.) was used to carry out ammonia adsorption testing for cobalt-cobalt cyanocomplex PCo1. After PCo1 was thermally treated at 100° C. for 24 hours, ammonia gas adsorption testing was performed. As a result, it has been found that the amount of adsorption of ammonia at 1 atm is about 24 mmol/g. The results are illustrated in FIG. 9. For comparison purposes, FIG. 9 also shows the results of using ion exchange resin set forth in Non-Patent Publication 5 (Amber Lyst 15: Sigma-Aldrich Co., Ltd.), zeolite (13X zeolite WE894: Baylith Co., Ltd.) and activated carbon (activated carbon 1.09624: Merck Co., Ltd.). It has thus been found that PCo1 ($Co[Co(CN)_6]_{0.67}$) has an adsorption capacity of more than twice that of the existing adsorbents.

APPLICABILITY TO THE INDUSTRY

According to the invention, it is possible to obtain an ammonia adsorbent having a variety of functions added to it through material selection. This ammonia adsorbent may find applications in the form of ammonia occlusion materials, ammonia sensors, ammonia removal filters, ammonia recovery apparatuses and so on, so contributing more to energy storage, environmental cleaning, waste liquid disposal, exhaust gas disposal, etc.

What is claimed is:

1. A method for adsorption of ammonia molecules, comprising:
    contacting a gas containing ammonia molecules ($NH_3$) with a metal cyanocomplex represented by a general formula: $A_xM[M'(CN)_6]_y.zH_2O$,
    where M stands for copper, or copper and one or more metal atoms selected from the group consisting of vanadium, chromium, manganese, iron, ruthenium, cobalt, rhodium, nickel, palladium, platinum, silver, zinc, lanthanum, europium, gadolinium, lutetium, barium, strontium, and calcium,
    M' stands for iron, or iron and one or more metal atoms selected from the group consisting of vanadium, chromium, molybdenum, tungsten, manganese, ruthenium, cobalt, nickel, platinum, and copper,
    A stands for potassium cations, or potassium cations and one or more cations selected from the group consisting of hydrogen, lithium, sodium, rubidium, and cesium,
    x stands for a numerical value from 0 to 3,
    y stands for a numerical value from 0.1 to 1.5, and
    z stands for a numerical value from 1 to 6,
    thereby allowing for adsorption of the ammonia molecules in said gas, wherein said metal cyanocomplex is recovered by allowing for desorption of the ammonia molecules from said metal cyanocomplex, thereby recovering said metal cyanocomplex.

2. A method for adsorption of ammonia molecules as recited in claim 1, further comprising, upon contact with said gas containing ammonia molecules, applying a pressure to said gas thereby increasing an amount of adsorption.

3. A method for recovery of a metal cyanocomplex, further comprising, after adsorption of the ammonia molecules onto said metal cyanocomplex by the method as recited in claim 1,
immersing said metal cyanocomplex in water, an aqueous acid solution or an aqueous salt solution, or
heating said metal cyanocomplex, or
irradiating said metal cyanocomplex with ultraviolet rays,
thereby allowing for the desorption of the ammonia molecules from said metal cyanocomplex.

4. A method for adsorption of ammonia molecules as recited in claim 1, wherein the metal cyanocomplex has a reduction potential of +0 volt or lower on a hydrogen standard electrode basis so that the ammonia molecules are occluded in said metal cyanocomplex.

5. A method for adsorption of ammonia molecules as recited in claim 1, wherein the metal cyanocomplex has a reduction potential higher than −0.1 volt and lower than +1.5 volts on a hydrogen standard electrode basis so that decomposition of the ammonia molecules adsorbed takes place.

6. A method for recovery of a metal cyanocomplex, further comprising, after decomposition of the ammonia molecules adsorbed onto said metal cyanocomplex by the method as recited in claim 5, leaving said metal cyanocomplex to stand in an atmosphere thereby restoring said metal cyanocomplex back to a before-adsorption state.

7. A method for adsorption of ammonia molecules as recited in claim 1, wherein said metal cyanocomplex is carried on a fiber or yarn, or a woven or an unwoven fabric.

8. A method for adsorption of ammonia molecules, comprising:
contacting a gas containing ammonia molecules ($NH_3$) with a metal cyanocomplex represented by a general formula: $A_xM[M'(CN)_6]_y \cdot zH_2O$,
where M stands for copper, or copper and one or more metal atoms selected from the group consisting of vanadium, chromium, manganese, iron, ruthenium, cobalt, rhodium, nickel, palladium, platinum, silver, zinc, lanthanum, europium, gadolinium, lutetium, barium, strontium, and calcium, M' stands for iron, or iron and one or more metal atoms selected from the group consisting of vanadium, chromium, molybdenum, tungsten, manganese, ruthenium, cobalt, nickel, platinum, and copper,
A stands for potassium cations, or potassium cations and one or more cations selected from the group consisting of hydrogen, lithium, sodium, rubidium, and cesium,
x stands for a numerical value from 0 to 3,
y stands for a numerical value from 0.1 to 1.5, and
z stands for a numerical value from 0 to 6,
thereby allowing for adsorption of the ammonia molecules in said gas.

9. A method for adsorption of ammonia molecules as recited in claim 8, further comprising, upon contact with said gas containing ammonia molecules, applying a pressure to said gas thereby increasing an amount of adsorption.

10. A method for recovery of a metal cyanocomplex, further comprising, after adsorption of the ammonia molecules onto said metal cyanocomplex by the method as recited in claim 8,
immersing said metal cyanocomplex in water, an aqueous acid solution or an aqueous salt solution, or
heating said metal cyanocomplex, or
irradiating said metal cyanocomplex with ultraviolet rays,
thereby allowing for the desorption of the ammonia molecules from said metal cyanocomplex.

11. A method for adsorption of ammonia molecules as recited in claim 8, wherein the metal cyanocomplex has a reduction potential of +0 volt or lower on a hydrogen standard electrode basis so that the ammonia molecules are occluded in said metal cyanocomplex.

12. A method for adsorption of ammonia molecules as recited in claim 8, wherein the metal cyanocomplex has a reduction potential higher than −0.1 volt and lower than +1.5 volts on a hydrogen standard electrode basis so that decomposition of the ammonia molecules adsorbed takes place.

13. A method for recovery of a metal cyanocomplex, further comprising, after decomposition of the ammonia molecules adsorbed onto said metal cyanocomplex by the method as recited in claim 12, leaving said metal cyanocomplex to stand in an atmosphere thereby restoring said metal cyanocomplex back to a before-adsorption state.

14. A method for adsorption of ammonia molecules as recited in claim 8, wherein said metal cyanocomplex is carried on a fiber or yarn, or a woven or unwoven fabric.

* * * * *